Figure 1:
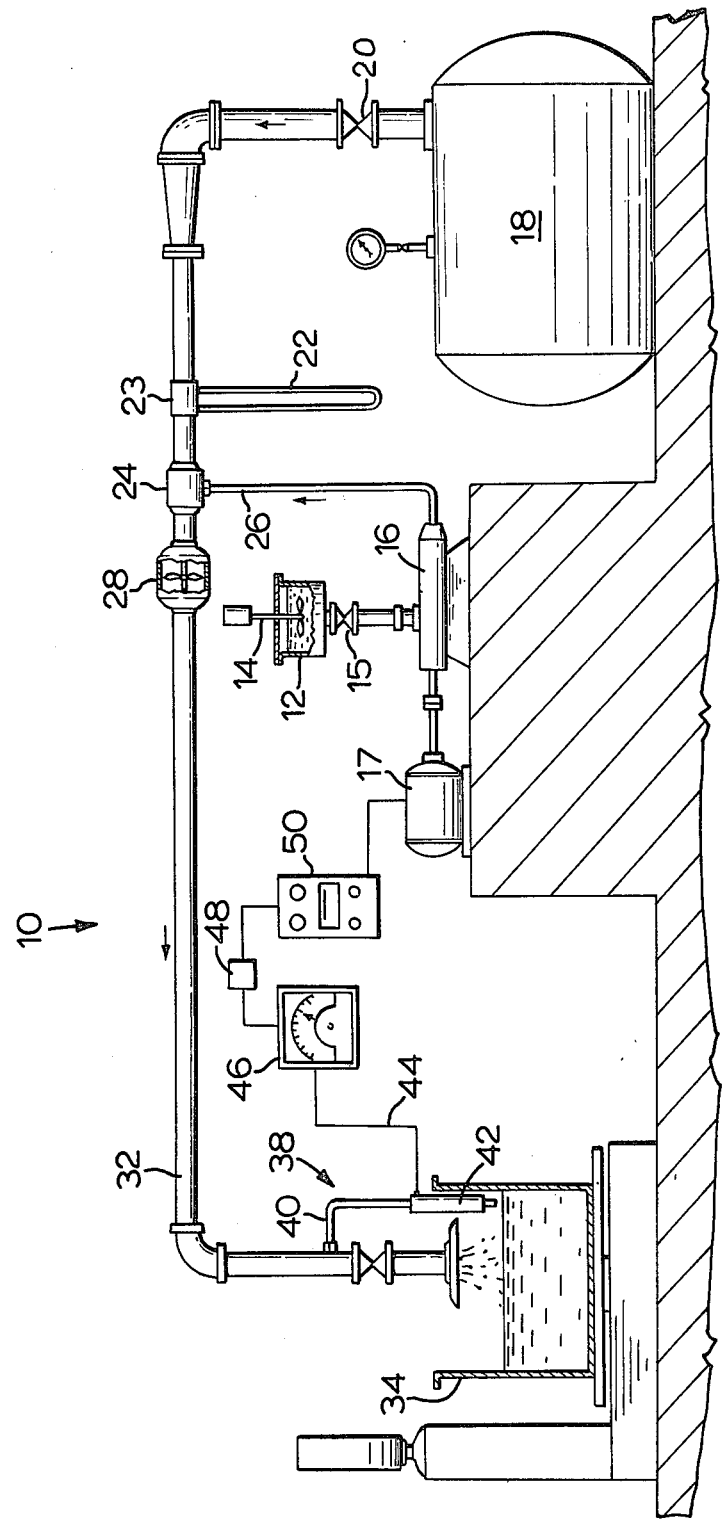

United States Patent [19]

Akgungor et al.

[11] 4,024,883
[45] May 24, 1977

[54] FLOW ADDITIVE SUSPENSION SYSTEM

[75] Inventors: Ali Caglar Akgungor, Lachine; Ertugrul Bilgen, Pointe Claire, both of Canada

[73] Assignee: Canadian General Electric Company Limited, Toronto, Canada

[22] Filed: Oct. 31, 1973

[21] Appl. No.: 411,213

[30] Foreign Application Priority Data

Dec. 8, 1972 Canada .............................. 158494

[52] U.S. Cl. ..................................... 137/5; 137/13; 137/93; 252/314; 252/359 A
[51] Int. Cl.² ......................................... F17D 1/16
[58] Field of Search ........... 252/314, 8.55 R, 8.5 C; 137/13, 5, 93; 259/149, 154

[56] References Cited

UNITED STATES PATENTS

| | | | |
|---|---|---|---|
| 1,145,509 | 7/1915 | Pike et al. .............................. | 137/5 |
| 2,593,825 | 4/1952 | Albrecht ............................... | 137/93 |
| 2,626,620 | 1/1953 | Smith .................................... | 137/93 |
| 2,663,308 | 12/1953 | Hodgens ............................... | 137/93 |
| 3,102,548 | 9/1963 | Smith et al. .......................... | 137/13 |
| 3,146,200 | 8/1964 | Goldstein et al. ............ | 252/8.55 X |
| 3,254,719 | 6/1966 | Root .................... | 166/308 |
| 3,361,213 | 1/1968 | Savins .............. | 137/13 X |
| 3,408,296 | 10/1968 | Kuhn et al. ........................ | 252/8.55 |
| 3,710,811 | 1/1973 | Leverenz et al. ...................... | 137/5 |

Primary Examiner—Herbert B. Guynn
Attorney, Agent, or Firm—Raymond A. Eckersley

[57] ABSTRACT

Long chain polymer flow promoting additives including guar gum, polyethylene oxide and polyacrylamide used to maintain Newtonian flow characteristics in an extended velocity range are mixed into a neutral density liquid having a significant variation of electrical conductivity with the dilution of the neutral density liquid, to provide a stable additive mixture. The concentration of the neutral density carrier liquid when diluted as a working liquid in use within a machine or system may be readily determined by measuring the electrical conductivity of the working liquid, thus permitting the working liquid content of flow promoting additive to be readily determined and controlled.

4 Claims, 1 Drawing Figure

FLOW ADDITIVE SUSPENSION SYSTEM

This invention is directed to a flow control system and in particular to a method and apparatus for mixing and controlling the working concentration of flow-promoting additive.

The use of a family of long chain polymer materials for suppressing the incidence of turbulent flow in liquids is well known. Such materials as polyethylene oxide (PEO), polyacrylamide and guar gum are known to promote streamline Newtonian flow for velocities considerably in excess of turbulent flow velocity at normal conditions.

The use of such flow promoting materials is hampered by the difficulties involved in making available mixtures of the flow promoting additive at desired concentrations, and in monitoring the subsisting concentration of the additive in the working liquid.

An object of the present invention is to provide a flow control system for mixing a flow promoting long chain additive in a quantitively analyzable liquid, to permit ready determination of additive concentration when diluted by a working liquid. A further object is the provision of a non-poisonous carrier liquid for mixing with the long chain additive.

A further object of the invention is to provide mixing of flow promoting additive in a low cost liquid carrier, to form a stable, pumpable mixture.

A further object of the present invention is to mix flow promoting additive with a liquid in a stable, substantially non-settling mixture.

A further object of the present invention is to provide a mixture of flow promoting additive in a predetermined range of concentration, to form a neutral density mixture with a mixing liquid.

In using long chain flow promoting additives such as polyethylene oxide (PEO), polyacrylamide or guar gum considerable problems have been encountered in mixing the material in a suitable liquid to permit ready application thereof in a desired environment such as a water turbine or a pipe line. While various solvents or mixtures may be used, problems arise in pumping the mixture, and in maintaining stability of the mixture without the occurrence of settling out of the additive or degradation of its streamline flow promoting characteristics. Additionally, the mixture of additive and its carrier liquid must be in a concentration suited to the proposed use of the material in promoting streamline flow.

It will be understood that the term "mixing" as used in this disclosure covers:

1. the case where the related additive is a nonsolvent in the mixing liquid, being in suspension;
2. the case where the additive is in solution; and
3. the case where additive dissolved in a solvent is additionally diluted.

In order to provide a perspective on a possible commercial use of a flow promoting additive, for instance the operation of a 50 megawatt hydraulic turbine, an injection rate of 6 lbs of additive per hour would be realistic. Using an optimized 20% slurry suspension concentration (i.e. 200,000 parts per million by weight; 200,000 w.p.p.m.) this injection rate requires 30 lb/hr of slurry i.e. 0.5 lb/minute.

Certain embodiments of the invention are described, reference being made to the accompanying drawing which shows a mixing, diluting and concentration metering arrangement as disclosed hereafter.

It has been found that PEO can be effectively suspended in a neutral density suspension using sodium chloride (NaCl) as a 25% solution by weight, being substantially totally soluble.

In the case of guar gum and polyacrylamide, suspension as a neutral density suspension is achieved using 30% by weight sodium carbonate ($Na_2CO_3$) in water, wherein successful suspension as a non-solvent is achieved in a few minutes.

However, in order to achieve a sufficient subsequent rate of dispersion of the suspension when using the neutral solution, the optimum slurry concentration for rapid dispersion to a working concentration is about 5% by weight.

In cases when the slurry is to be injected into high velocity work zones where mixing is rapidly promoted, such as the shroud space of a Francis turbine, then higher slurry concentrations, in the order of, say, 20% by weight may be effectively used.

It has further been found that using a mechanical mixing device such as a mixing propeller, the subject flow promoting materials can be uniformly dispersed in the selected neutral density salt solution. Furthermore, the mixture is very stable, having a low rate of precipitation, and requiring minimal stirring to offset any tendency to settle out, as a result of local, thermally induced convection currents. Owing to the substantially consistent homogeneity thus readily achieved, the content of flow promoting material in a neutral salt solution of known salinity can be directly related to the saline content of the mixture. Thus, in the case where a starting mixture of known saline and additive concentration is diluted to an unknown extent in a working liquid, the content of flow promoting material in the working liquid may be readily and accurately determined as an analog of the saline content of the working liquid. The determination of saline content can be readily ascertained using an electrical conductivity determination, permitting about 90% accuracy of determination. The successful functioning of the subject flow promoting additive is not critically dependent on correct concentration within this limit of accuracy. However, it is desirable both from the need to avoid needless pollution, and the desire to achieve low costs and high system efficiency by using minimal quantities of additive, to monitor additive concentration as accurately as possible, which the system makes possible.

Referring to the drawing, this shows a laboratory test system for demonstrating the functioning of the invention. The illustrated system 10 has a slurry tank 12 to contain a known concentration of selected flow promoting additive in its disclosed neutral gravity solution. A low power low speed propeller type stirrer 14 provides limited stirring to maintain the mixture and to preclude settling out. A throttle valve 15 controls admission of the mixture to pump 16, which is a positive displacement swash plate type pump driven by motor 17.

A supply of working liquid, in this case fresh water is provided from a pressurized header tank 18, the discharge rate of which is controlled by valve 20.

A monometer 22 of an orifice flowmaker 23 is provided for checking the rate of flow of the working liquid.

An injector type mixing section 24 receives the working liquid and the mixed additive, entering at pipe 26.

Downstream of the mixing section 24 is located a propeller mixer 28 to ensure complete dilution of the additive mixture into the working liquid. In the case of a practical embodiment such as a turbine, the naturally occurring flow pattern within the machine may be relied upon to provide requisite dilution of the additive mixture to working concentration.

The treated working liquid passes by way of pipe 32 to a weighing tank 34, serving to provide a weight check of the system output.

A concentration monitoring arrangement 38 includes a sampling tap 40 connecting the pipe 32 with an epoxy flow cell 42. The epoxy flow cell 42 provides a conductivity signal by connection 44 to a conductivity meter 46 connected in switching relation with the pump motor 17 through an on-off relay 48, and constant speed control 50.

The flow cell 42 detects the salinity of the working liquid in pipe 32, which is registered on the meter 46 and gives an analog of the additive concentration. This is used as a feedback signal to control the admission of further additive mixture in the system. In operating the system it is necessary to control the rate of mixing of the additives to their respective neutral solutions, to avoid local high temperatures that can cause chemical degredation of the additive. This stems from the low thermal conductivities, which lead to wide variations in shear stress while mixing.

What I claim as new and desire to secure by Letters Patent of the United States is:

1. The process of adding to a main body of water an additive substance in predetermined concentration as a stable quantitively determinable liquid mixture selected from the group consisting of quar gum, and polyacrylamide and polyethylene oxide having the property of maintaining Newtonian flow characteristics in an extended flow velocity range, by mixing said selected additive substance in a liquid vehicle suited for selective dosage administration, including the steps of bringing together a mass of said selected substance in controlled mechanical dispersion with a mass of compatible mixing liquid having substantially neutral density in relation thereto, and possessing a determinable electrical characteristic related to the concentration thereof, said compatible mixing liquid being a salt solution consisting of a 25% by weight solution of sodium chloride in water where said additive substance is polyethylene oxide and a 30% by weight solution of sodium carbonate in water where said additive substance is guar gum or polyacryamide, turbulating the components to provide a substantially homogeneous stable and pumpable mixture having a low rate of precipitation, diluting the substance to a further extent by addition thereof to said main body of water, determining the electrical conductivity of the diluted mixture as an analog of the content of said additive substance and using said conductivity as a feed back signal to control the rate of addition of said mixture in response to the signal to achieve a desired concentration of said additive in said main body of water.

2. The process according to claim 1 wherein said pumpable mixture comprises a slurry having of said guar gum or polyacrylamide in suspension in a 30% by weight sodium carbonate solution.

3. The process according to claim 1 wherein said pumpable mixture comprises a slurry having polyethylene oxide dissolved in a 25% by weight sodium chloride solution.

4. The process according to claim 3 wherein said pumpable mixture is diluted by injection as a slurry into a high turbulence region of a working liquid, to promote effective mixing therebetween.

* * * * *

UNITED STATES PATENT OFFICE
CERTIFICATE OF CORRECTION

PATENT NO. : 4,024,883
DATED : May 24, 1977
INVENTOR(S) : Ali Caglar Akgungor & Ertugrul Bilgen It is certified that error appears in the above-identified patent and that said Letters Patent are hereby corrected as shown below:

First printed page -"Assignee: Canadian General Electric Company Limited, Toronto, Ontario, Canada."

Should be - "Assignee: Dominion Engineering Works Limited, Quebec, Canada"

Signed and Sealed this

Fourth Day of October 1977

[SEAL]

Attest:

RUTH C. MASON
Attesting Officer

LUTRELLE F. PARKER
Acting Commissioner of Patents and Trademark